United States Patent
Chueh et al.

(10) Patent No.: US 9,402,876 B2
(45) Date of Patent: Aug. 2, 2016

(54) METHOD AND PHARMACEUTICAL COMPOSITION FOR HAIR GROWTH

(71) Applicant: INDUSTRIAL TECHNOLOGY RESEARCH INSTITUTE, Hsinchu (TW)

(72) Inventors: Shan Chang Chueh, Taipei (TW); Ching Huai Ko, Changhua County (TW); Nien Tzu Chou, Hsinchu (TW); Cheng Ming Chuong, Irvine, CA (US); Chih Chiang Chen, Taipei (TW)

(73) Assignees: INDUSTRIAL TECHNOLOGY RESEARCH INSTITUTE, Hsinchu (TV); UNIVERSITY OF CALIFORNIA, Los Angeles, CA (US)

( * ) Notice: Subject to any disclaimer, the term of this patent is extended or adjusted under 35 U.S.C. 154(b) by 0 days.

(21) Appl. No.: 14/494,514

(22) Filed: Sep. 23, 2014

(65) Prior Publication Data
US 2015/0148300 A1 May 28, 2015

(30) Foreign Application Priority Data

Nov. 27, 2013 (TW) .............................. 102143165 A
Jul. 8, 2014 (CN) .......................... 2014 1 0322734
Jul. 8, 2014 (TW) .............................. 103123412 A (51) Int. Cl.
| | | |
|---|---|---|
| C07K 7/06 | (2006.01) |
| A61K 38/10 | (2006.01) |
| C07K 7/08 | (2006.01) |
| A61K 9/00 | (2006.01) |

(52) U.S. Cl.
CPC .............. *A61K 38/10* (2013.01); *A61K 9/0014* (2013.01); *C07K 7/08* (2013.01)

(58) Field of Classification Search
CPC ....... A61K 38/03; A61K 38/04; A61K 38/10; C07K 7/08; C07K 7/08
See application file for complete search history.

(56) References Cited

U.S. PATENT DOCUMENTS

| | | | |
|---|---|---|---|
| 5,470,876 A | 11/1995 | Proctor |
| 5,550,183 A | 8/1996 | Pickart |
| 5,587,457 A | 12/1996 | Rathjen et al. |
| 5,739,111 A | 4/1998 | Mahe |
| 6,303,576 B1 | 10/2001 | Blaschuk et al. |
| 6,375,928 B1 | 4/2002 | Rathjen et al. |
| 6,451,759 B1 | 9/2002 | Kang et al. |
| 6,531,290 B2 | 3/2003 | Dalie et al. |
| 7,138,264 B1 | 11/2006 | Beyer et al. |
| 7,256,254 B2 | 8/2007 | Zimmerman |
| 7,361,485 B2 | 4/2008 | Verheijen et al. |
| 7,529,628 B2 | 5/2009 | Beyer et al. |
| 7,824,897 B2 | 11/2010 | Beyer et al. |
| 8,106,017 B2 | 1/2012 | Chung et al. |
| 8,298,537 B2 | 10/2012 | Feldmann et al. |
| 2007/0129284 A1* | 6/2007 | Kjeldsen et al. ................. 514/3 |
| 2009/0092663 A1* | 4/2009 | Ponzoni et al. ............... 424/450 |

FOREIGN PATENT DOCUMENTS

| | | |
|---|---|---|
| TW | 58330 | 5/1984 |
| TW | 74578 | 2/1986 |
| TW | 200509957 | 3/2005 |
| TW | 200509972 | 3/2005 |
| TW | 200539897 | 12/2005 |
| TW | 200612904 | 5/2006 |
| TW | I278313 | 4/2007 |
| TW | 200800243 | 1/2008 |
| TW | 200804592 | 1/2008 |
| TW | 200927161 | 7/2009 |
| TW | 201129368 | 9/2011 |
| TW | I353249 | 12/2011 |
| TW | I353849 | 12/2011 |
| WO | 2010059861 | 5/2010 |
| WO | 2010059862 | 5/2010 |

OTHER PUBLICATIONS

Stefanie Gilles, Release of TNF-a during myocardial reperfusion depends on oxidative stress and is prevented by mast cell stabilizers, Cardiovascular Research 60 (2003) 608-616.*
UniProt Protein Databse, Protein Accession C1K3N5, Tumor Necrosis factor alpha, accessed on Jan. 9, 2015, pp. 1-8.*
SIGMA, 2004, pp. 1-2.*
Rudinger, Peptide Hormones, JA Parsons, Ed., 1976, pp. 1-7.*
Yoshiyuki Tanabe, Purification of Recombinant Human Tumor Necrosis Factor Precursor From Escherichza Colz, Biochemical and Biophysical Research Communications, vol. 179, No. 1, 1991, pp. 683-688.*
UniProt Protein Database, Protein Accession P01375, Tumor Necrosis Factor, accessed Sep. 15, 2015.*
Marcus Maurer et al., Activated skin mast cells are involved in murine hair follicle regression, Laboratory Investigation, Oct. 1997, p. 319-332, vol. 77 No. 4.
Sven Muller-Rover et al., A Comprehensive Guide for the Accurate Classication of Murine Hair Follicles in Distinct Hair Cycle Stages, Journal of Investigative Dermatology, 117:3-15, 2001.
Maksim V. Plikus et al., Analyses of regenerative wave patterns in adult hair follicle populations reveal macro-environmental regulation of stem cell activity, Int J Dev Biol. 2009 ; 53(5-6): 857-868.
W. Gebhart et al., Cyclosporin-A-Induced Hair Growth in Human Renal AHograft Recipients and Alopecia Areata, Arch Dermatol Res (1986) 278:238-240.
Wael I. Al-Daraji et al., Localization of Calcineurin/NFAT in Human Skin and Psoriasis and Inhibition of Calcineurin/FAT Activation in Human Keratinocytes by Cyclosporin A, J Invest Dermatol 118:779-788, 2002.

(Continued)

*Primary Examiner* — James H Alstrum Acevedo
*Assistant Examiner* — Erinne Dabkowski
(74) *Attorney, Agent, or Firm* — WPAT, P.C. Intellectual Property Attorneys; Anthony King (57) ABSTRACT

The present disclosure relates to a method and a pharmaceutical composition for hair growth. The pharmaceutical composition includes a hair growth peptide (HGP) which includes all or part of the amino acid sequence SEQ ID No: 1. The method includes administering a hair growth peptide (HGP) which includes all or part of the amino acid sequence SEQ ID No: 1 to a party of interest.

4 Claims, 4 Drawing Sheets

(56) References Cited

OTHER PUBLICATIONS

Michael Taylor et al., Cyclosporin A prolongs human hair growth in vitro, J Invest Dermatol 100:237-239, 1993.
Akio Shirai et al., Topical application of cyclosporin A induces rapid-remodeling of damaged anagen hair follicles produced in cyclophosphamide administered mice, Journal of Dermatological Science 27 (2001) 7-13.
Wenrong Xue et al., Cyclosporine A stimulated hair growth from mouse vibrissae follicles in an organ culture model, Journal of Biomedical Research, 2012, 26(5): 372-380.
Tomoya Takahashi et al., Cyclosporin A Promotes Hair Epithelial Cell Proliferation and Modulates Protein Kinase C Expression and Translocation in Hair Epithelial Cells, J Invest Dermatol 117:605-611, 2001.
Anat Gafter-Gvili et al., Cyclosporin A-induced hair growth in mice is associated with inhibition of calcineurin-dependent activation of NFAT in follicular keratinocytes, Am J Physiol Cell Physiol 284:C1593-C1603, 2003.
Chang Deok Kim et al., Induction of synapse associated protein 102 expression in cyclosporin A-stimulated hair growth, Experimental Dermatology 2008; 17: 693-699.
Maksim V. Plikus et al., Self-Organizing and Stochastic Behaviors During the Regeneration of Hair Stem Cells, Science. Apr. 29, 2011; 332(6029): 586-589.
Maksim V. Plikus et al.,Cyclic dermal BMP signalling regulates stem cell activation during hair regeneration, vol. 451, Jan. 17, 2008.
Sam J. Mathew et al., Looking beyond death: a morphogenetic role for the TNF signalling pathway, Journal of Cell Science 122, 1939-1946.
M.H. Kwack et al., I-Ascorbic acid 2-phosphate promotes elongation of hair shafts via the secretion of insulin-like growth factor-1 from dermal papilla cells through phosphatidylinositol 3-kinase, British Journal of Dermatology 2009 160, pp. 1157-1162.
Johanna Laurikkala et al., TNF Signaling via the Ligand- Receptor Pair Ectodysplasin and Edar Controls the Function of Epithelial Signaling Centers and Is Regulated by Wnt and Activin during Tooth Organogenesis, Developmental Biology 229, 443-455 (2001).
Yuhang Zhang et al., Reciprocal requirements for EDA/EDAR/NF-kappaB and Wnt/beta-catenin signaling pathways in hair follicle induction, Developmental Cell 17, 49-61, Jul. 21, 2009.
Ran Brosh et al., p53-dependent transcriptional regulation of EDA2R and its involvement in chemotherapy-induced hair loss, FEBS Letters 584 (2010) 2473-2477.
Charlene S. L. Hoi et al., Runx1 Directly Promotes Proliferation of Hair Follicle Stem Cells and Epithelial Tumor Formation in Mouse Skin, Molecular and Cellular Biology, vol. 30, No. 10, May 2010, p. 2518-2536.
Denis J. Headon et al., Involvement of a novel Tnf receptor homologue in hair follicle induction, Nature Genetics, pp. 370-374, vol. 22, Aug. 1999.
Chang-Yi Cui et al., Dkk4 and Eda Regulate Distinctive Developmental Mechanisms for Subtypes of Mouse Hair, PLoS ONE, vol. 5(4), Apr. 2010, e10009.
Tetsuo Kojima et al., TROY, a newly identified member of thetumor necrosis factor receptor superfamily, exhibits a homology with Edar and is expressed in embryonic skin and hair follicles, J. Biol. Chem. 2000, 275:20742-20747.
Saskia Lippens et al., Keratinocyte-specific ablation of the NF-kB regulatory protein A20 (TNFAIP3) reveals a role in the control of epidermal homeostasis, peer-00640518, version 1, Nov. 13, 2011.
Marja L. Mikkola, TNF superfamily in skin appendage development, Cytokine & Growth Factor Reviews 19 (2008) 219-230.
Xuemei Tong et al., Keratin 17 modulates hair follicle cycling in a TNF alpha-dependent fashion, Genes & Development 20:1353-1364, 2006.
Johanna Laurikkala et al., Regulation of hair follicle development by the TNF signal ectodysplasin and its receptor Edar, Development 129, 2541-2553 (2002).
Rebecca P. Hill et al., Human hair follicle dermal cells and skin fibroblasts show differential activation of NF-jB in response to pro-inflammatory challenge, Experimental Dermatology, 21, 2011, 154-160.
Randall B. Widelitz et al., FGF induces new feather buds from developing avian skin, J Invest Dermatol 107:797-803, 1996.
Paul T. Sharpe, Fish scale development: Hair today, teeth and scales yesterday?, Current Biology, 2001, vol. 11, No. 18, pp. R751-R752.
Johanna Pispa et al., Edar and Troy signalling pathways act redundantly to regulate initiation of hair follicle development, Human Molecular Genetics, 2008, vol. 17, No. 21, 3380-3391.
Xu Yongan et al., Development of Hair Follicle Stem Cells Related Signal Transduction in Proliferation and Differentiation, Chinese Journal of Reparative and Reconstructive Surgery, February -162-2010, vol. 24, No. 2, pp. 161-164.
English translation of foreign reference I278313 and I353849.
Office action and search report dated Jun. 2, 2015 for the Taiwan counterpart application 103123412.
English abstract translation of the Office action dated Jun. 2, 2015 for the Taiwan counterpart application 103123412.
English translation of the Search report dated Jun. 2, 2015 for the Taiwan counterpart application 103123412.
Emi Hifumi et al,, Catalytic digestion of human tumor necrosis factor-beta by antibody heavy chain, FEBS Journal 227, 2010, pp. 3823-3832.
Heng Hsin Co., Ltd., Innophos, Innovate with Phosphate, Feb. 1, 2010.
Jiro Kishimoto, et al., Wnt signaling maintains the hair-inducing activity of the dermal papilla, Genes Dev., 2000, 14: 1181-1185.
Elaine Fuchs, et al., At the Roots of a Never-Ending Cycle, Developmental Cell, vol. 1, Jul. 13-25, 2001.
Sarah E. Millar, Molecular Mechanisms Regulating Hair Follicle Development. The Journal of Investigative Dermatology, vol. 118, No. 2A Feb. 2002.

* cited by examiner

ID No: 1) are 90% to 99%. The similarity is obtained by the software shimadu LCMS2010 for sequence analysis.

```
SEQUENCE LISTING

<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 1

Ser Pro Leu Ala Gln Ala Val Arg Ser Ser Ser Arg
1               5                   10

<210> SEQ ID NO 2
<211> LENGTH: 5
<212> TYPE: PRT
<213> ORGANISM: Artificial Sequence
<220> FEATURE:
<223> OTHER INFORMATION: a designed peptide according to experiments

<400> SEQUENCE: 2

Val Arg Ser Ser Ser
1               5

<210> SEQ ID NO 3
<211> LENGTH: 5
<212> TYPE: PRT
<213> ORGANISM: Artificial Sequence
<220> FEATURE:
<223> OTHER INFORMATION: a designed peptide according to experiments

<400> SEQUENCE: 3

Ser Pro Leu Ala Gln
1               5

<210> SEQ ID NO 4
<211> LENGTH: 15
<212> TYPE: PRT
<213> ORGANISM: Artificial Sequence
<220> FEATURE:
<223> OTHER INFORMATION: a designed peptide according to experiments

<400> SEQUENCE: 4

Ser Pro Leu Ala Gln Ala Val Arg Ser Ser Ser Arg Thr Pro Ser
1               5                   10                  15

<210> SEQ ID NO 5
```

```
<211> LENGTH: 5
<212> TYPE: PRT
<213> ORGANISM: Artificial Sequence
<220> FEATURE:
<223> OTHER INFORMATION: a designed peptide according to experiments

<400> SEQUENCE: 5

Arg Ser Ser Ser Arg
1               5

<210> SEQ ID NO 6
<211> LENGTH: 11
<212> TYPE: PRT
<213> ORGANISM: Artificial Sequence
<220> FEATURE:
<223> OTHER INFORMATION: a designed peptide according to experiments

<400> SEQUENCE: 6

Ser Pro Leu Ala Gln Ala Val Arg Ser Ser Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: a designed peptide according to experiments

<400> SEQUENCE: 7

Ser Pro Leu Ala Gln Ala Val Arg Ser Ser
1               5                   10

<210> SEQ ID NO 8
<211> LENGTH: 9
<212> TYPE: PRT
<213> ORGANISM: Artificial Sequence
<220> FEATURE:
<223> OTHER INFORMATION: a designed peptide according to experiments

<400> SEQUENCE: 8

Ser Pro Leu Ala Gln Ala Val Arg Ser
1               5

<210> SEQ ID NO 9
<211> LENGTH: 8
<212> TYPE: PRT
<213> ORGANISM: Artificial Sequence
<220> FEATURE:
<223> OTHER INFORMATION: a designed peptide according to experiments

<400> SEQUENCE: 9

Ser Pro Leu Ala Gln Ala Val Arg
1               5

<210> SEQ ID NO 10
<211> LENGTH: 7
<212> TYPE: PRT
<213> ORGANISM: Artificial Sequence
<220> FEATURE:
<223> OTHER INFORMATION: a designed peptide according to experiments

<400> SEQUENCE: 10

Ser Pro Leu Ala Gln Ala Val
1               5

<210> SEQ ID NO 11
<211> LENGTH: 6
```

```
<212> TYPE: PRT
<213> ORGANISM: Artificial Sequence
<220> FEATURE:
<223> OTHER INFORMATION: a designed peptide according to experiments

<400> SEQUENCE: 11

Ser Pro Leu Ala Gln Ala
1               5

<210> SEQ ID NO 12
<211> LENGTH: 11
<212> TYPE: PRT
<213> ORGANISM: Artificial Sequence
<220> FEATURE:
<223> OTHER INFORMATION: a designed peptide according to experiments

<400> SEQUENCE: 12

Pro Leu Ala Gln Ala Val Arg Ser Ser Ser Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: a designed peptide according to experiments

<400> SEQUENCE: 13

Leu Ala Gln Ala Val Arg Ser Ser Ser Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: a designed peptide according to experiments

<400> SEQUENCE: 14

Ala Gln Ala Val Arg Ser Ser Ser Arg
1               5

<210> SEQ ID NO 15
<211> LENGTH: 8
<212> TYPE: PRT
<213> ORGANISM: Artificial Sequence
<220> FEATURE:
<223> OTHER INFORMATION: a designed peptide according to experiments

<400> SEQUENCE: 15

Gln Ala Val Arg Ser Ser Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: a designed peptide according to experiments

<400> SEQUENCE: 16

Ala Val Arg Ser Ser Ser Arg
1               5

<210> SEQ ID NO 17
<211> LENGTH: 6
<212> TYPE: PRT
```

```
<213> ORGANISM: Artificial Sequence
<220> FEATURE:
<223> OTHER INFORMATION: a designed peptide according to experiments

<400> SEQUENCE: 17

Val Arg Ser Ser Ser Arg
1               5

<210> SEQ ID NO 18
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 18

Ser Pro Leu Ala Gln Ala Val Arg Ser Ser Ser Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 19

Ser Pro Leu Ala Gln Ala Val Arg Ser Ser Gly Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 20

Ser Pro Leu Ala Gln Ala Val Arg Ser Gly Ser Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 21

Ser Pro Leu Ala Gln Ala Val Arg Gly Ser Phe Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 22

Ser Pro Leu Ala Gln Ala Val Gly Ser Phe Gly Ser
1               5                   10

<210> SEQ ID NO 23
<211> LENGTH: 12
<212> TYPE: PRT
<213> ORGANISM: Artificial Sequence
```

```
<220> FEATURE:
<223> OTHER INFORMATION: a designed peptide according to experiments

<400> SEQUENCE: 23

Ser Pro Leu Ala Gln Ala Gly Ser Phe Gly Ser Phe
1               5                   10

<210> SEQ ID NO 24
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 24

Ser Pro Leu Ala Gln Gly Ser Phe Gly Ser Phe Gly
1               5                   10

<210> SEQ ID NO 25
<211> LENGTH: 14
<212> TYPE: PRT
<213> ORGANISM: Artificial Sequence
<220> FEATURE:
<223> OTHER INFORMATION: a designed peptide according to experiments

<400> SEQUENCE: 25

Ser Pro Leu Ala Gln Ala Val Arg Ser Ser Ser Arg Thr Pro
1               5                   10

<210> SEQ ID NO 26
<211> LENGTH: 13
<212> TYPE: PRT
<213> ORGANISM: Artificial Sequence
<220> FEATURE:
<223> OTHER INFORMATION: a designed peptide according to experiments

<400> SEQUENCE: 26

Ser Pro Leu Ala Gln Ala Val Arg Ser Ser Ser Arg Thr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 27

Gly Pro Leu Ala Gln Ala Val Arg Ser Ser Ser Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 28

Gly Ser Leu Ala Gln Ala Val Arg Ser Ser Ser Arg
1               5                   10

<210> SEQ ID NO 29
<211> LENGTH: 12
<212> TYPE: PRT
<213> ORGANISM: Artificial Sequence
<220> FEATURE:
```

<223> OTHER INFORMATION: a designed peptide according to experiments

<400> SEQUENCE: 29

Gly Ser Phe Ala Gln Ala Val Arg Ser Ser Ser Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 30

Gly Ser Phe Gly Gln Ala Val Arg Ser Ser Ser Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 31

Gly Ser Phe Gly Ser Ala Val Arg Ser Ser Ser Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 32

Gly Ser Phe Gly Ser Phe Val Arg Ser Ser Ser Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 33

Ser Pro Leu Ala Gln Phe Arg Ser Ser Ser Arg Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 34

Leu Ala Gln Ala Gly Ser Val Arg Ser Ser Ser Arg
1               5                   10

<210> SEQ ID NO 35
<211> LENGTH: 12
<212> TYPE: PRT
<213> ORGANISM: Artificial Sequence
<220> FEATURE:
<223> OTHER INFORMATION: a designed peptide according to experiments

```
<400> SEQUENCE: 35

Ala Gln Ala Gly Ser Phe Val Arg Ser Ser Ser Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 36

Gln Ala Gly Ser Phe Gly Phe Arg Ser Ser Ser Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: a designed peptide according to experiments

<400> SEQUENCE: 37

Ala Gly Ser Phe Phe Ser Gly Arg Ser Ser Ser Arg
1               5                   10
```

METHOD AND PHARMACEUTICAL COMPOSITION FOR HAIR GROWTH The present application claims priority from Taiwanese applications Ser. Nos. 102143165 & 103123412 respectively filed on 27 Nov. 2013 & 8 Jul. 2014 and Chinese application Ser. No. 201410322734.1 filed on 8 Jul. 2014 of the same title and inventorship herewith.

TECHNICAL FIELD

The technical field relates to a method and a pharmaceutical composition for hair growth.

RELATED ARTS

Alopecia is a syndrome of loss of hair resulting from the decrease of hairs in the anagen phase of a hair growth cycle and from the increase of hairs in the catagen phase or telogen phase of the hair growth cycle. Although the mechanism of alopecia is unclear, a lot of factors causing alopecia might be endocrine disorder, hormone unbalance, autonomic nerves disorder, circular disorder, excessive sebum due to the abnormal blood circulation, degeneration of skin due to fungi, allergy, genetic disorder, or aging.

Alopecia is one of most serious side effects in cancer that is induced by various chemotherapeutic agents. Since these chemotherapeutic agents interrupt cytokinesis, the chemotherapeutic agents will induce side effects in the tissues, where cytokinesis frequently occurs, including bone marrow, hair follicle, fingernail, toenail, skin and gastrointestinal tract. Thus, the chemotherapeutic agents induce alopecia. Most of patients (80% or above) regard alopecia as the most painful effect in their chemotherapy. The need for treating alopecia due to the chemotherapy is still strong and not fulfilled.

Alopecia occurs in two to four weeks after the treatment of chemotherapy. Hair will grow during three to six months after the chemo-treatment. The degree of alopecia depends on the types of chemotherapeutic agents, the dosage thereof and the schedule of administration. Those agents inducing serious alopecia include cyclophosphamide, doxorubicin, cisplatin, cytosine arabinoside and etoposide. The above-mentioned agents induce alopecia even if those are administrated in partial area of the skin. In other words, the chemotherapeutic agents affect the cytokinesis of the hair follicle that induces apoptosis of the follicle cells or converts the anagen phase of the follicle cells into the catagen phase.

Currently, the clinic approaches for alopecia includes applying external medicine on the hair follicle, orally administrating medicine, and hair implantation. Minoxidil and Finasteride are two kinds of medicine for growth hair that are approved by FDA. Patients with alopecia are often required to continuously administrate Minoxidil for external use and the Finasteride for internal use. In addition, Minoxidil and Finasteride may only reduce the loss of hair instead of increasing the number of hair follicles. Moreover, since Minoxidil and Finasteride have several side effects such as sexual dysfunction, hypertrichosis, and fetus defect, none of the medicines can be administrated for pregnant women. Furthermore, hair implantation may leave scars, require a long recovering period, and cost a lot due to several times of surgery.

SUMMARY

The present disclosure provides a method for hair growth. The peptide is a hair growth peptide (HGP), which includes all or part of an amino acid sequence: SPLAQAVRSSSR (SEQ ID No: 1).

The present disclosure provides a method for hair growth. The peptide is HGP. A similarity between a sequence of the HGP and an amino acid sequence SPLAQAVRSSSR (SEQ ID No: 1) are 90% to 99%. The similarity is obtained by the software shimadu LCMS2010 for sequence analysis.

The present disclosure provides a pharmaceutical composition for the treatment of alopecia. The pharmaceutical composition includes a hair growth peptide (HGP) and a phosphate salt. The HGP includes all or part of an amino acid sequence: SPLAQAVRSSSR (SEQ ID No: 1).

The present disclosure provides a pharmaceutical composition for the treatment of alopecia. The pharmaceutical composition includes a hair growth peptide (HGP) and a phosphate salt. A similarity between a sequence of the HGP and an amino acid sequence SPLAQAVRSSSR (SEQ ID No: 1) are 90% to 99%.

Another function of the present disclosure will be described at following paragraphs. Certain functions can be realized in present section, while the other functions can be realized in detailed description. In addition, the indicated components and the assembly can be explained and achieved by detail of the present disclosure. Notably, the previous explanation and the following description are demonstrated instead of limiting the scope of the present disclosure.

The foregoing has outlined rather broadly the features and technical benefits of the disclosure in order that the detailed description of the disclosure that follows may be better understood. Additional features and benefits of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the disclosure as set forth in the appended claims.

BRIEF DESCRIPTION OF THE DRAWINGS

The accompanying drawings, which are incorporated in and constitute a part of this specification, illustrate embodiments of the disclosure and, together with the description, serve to explain the principles of the invention.

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

A more complete understanding of the present disclosure may be derived by referring to the detailed description and claims when considered in connection with the Figures, where like reference numbers refer to similar elements throughout the Figures, and:

FIG. 3 illustrates a schematic view of a TCF reporter assay in HaCaT Keratinocyte cell line. TOP represents that the reporter gene has a functional binding site where β-catenin is bound. FOP represents that the functional binding site of the reporter gene is mutated and hence β-catenin cannot bind on the binding site and acts as a negative control. CTL represents that HaCaT Keratinocytes are not treated with any stimulant. iPept-2 means that HaCaT Keratinocytes are treated with the SEQ ID No: 1 peptide. In view of the relative luciferase activity, HaCaT Keratinocytes with the treatment of the SEQ ID No: 1 peptide is observed to increase the activity of β-catenin.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In addition, the following embodiments can be properly integrated to complete another embodiment. References to "modified embodiment," "the embodiment," "other embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may.

The present disclosure is directed to a method for hair growth and a pharmaceutical composition for the treatment of alopecia. In order to make the present disclosure completely comprehensible, detailed steps and structures are provided in the following description. Obviously, implementation of the present disclosure does not limit special details known by persons skilled in the art. In addition, known structures and steps are not described in details, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed embodiments, and is defined by the claims. The following description of the disclosure accompanies drawings, which are incorporated in and constitute a part of this specification, and illustrate embodiments of the disclosure, but the disclosure is not limited to the embodiments.

The molecular weights of the peptides and the hair growth peptide (HGP) of the present disclosure are confirmed, but not limited, by a mass spectrometry. For instance, the present disclosure utilizes Time-of-Flight mass spectrometry, Sciex QSTAR PULSAR Quadrupole (purchased from Applied Biosystems) to confirm the molecular weight. The sample in appropriate amount is dissolved in a formic acid solution to form a sample solution. Under a special condition, protease such as serine proteases, threonine proteases, cysteine proteases, aspartate proteases, glutamic proteases and metalloproteases are used to cut the sample into several fragments, which is dissolved in the formic acid solution in order to complete a sample solution. 5 μl of the sample is injected into the foregoing mass spectrometry. After the mass spectrometry completes the measurement, a spectrogram from the mass spectrometry is analyzed by software such as shimadu LCMS2010 to confirm the target peptide(s) in the spectrogram. An approach to verify the target peptide in the spectrogram is to check the mass-to-charge ratios of at least two peaks, which fall within the range of the target peptide. Another approach is to check the difference between the mass-to-charge ratio of the target peptide and the mass-to-charge ratio of the peaks in the spectrogram. For instance, the molecular weight of amino acid sequence SEQ ID No: 1 is 1258.42. When the peptide carries two electric charges, the mass-to-charge ratio is about 630.21 ((1258.42+2)/2). The mass-to-charge ratio (m/z) is equal to the total mass (including the mass M of peptide and the mass N of the electron) divided by total electric charge. Thus, while the peak labeled with a mass-to-charge ratio about 630.21 is found in the spectrogram, it is confirmed that the peptide, which has an amino acid sequence the same with the SEQ ID No: 1 sequence, exists in the sample solution. In addition, the molecular weights of other amino acid sequences are listed in Table 1.

Similarly, the sample solution of the pharmaceutical composition is prepared by the above-identified process to confirm whether the peptide exists in the pharmaceutical composition. In some embodiments, the sample solution of the pharmaceutical composition is diluted before the foregoing process.

The phosphate salt of the pharmaceutical composition in the present disclosure is selected from $KH_2PO_4$, $Na_2HPO_4.2H_2O$ and a combination thereof.

In some embodiments, the pharmaceutical composition of the present disclosure includes excipients, which increase the uniformity and stability of the composition and decrease the irritation and stink of the composition. The excipients of the present disclosure are non-toxic, non-irritant, non-antigenic, non-allergic, non-mutagenic and non-pharmacoactive and do not interfere pharmacodynamics of the composition.

Accordingly, the excipients of the present disclosure are selected from lactose, starch, starch paste, dextrin, cyclodextrin, pregelatinized starch, carboxymethyl starch sodium, hydroxypropyl starch, microcrystalline cellulose, carboxyl methyl cellulose, cross-linked carboxymethy cellulose sodium, low substituted hydroxypropyl cellulose and a combination of the at least two foresaid excipients.

The identification method for the excipients is selected from chromatography methods, spectrophotometry methods, spectroscopy methods and titrimetric methods.

The hair growth peptides (HGP) in the present disclosure or in the pharmaceutical composition are synthesized, but not limited, by the solid phase peptide synthesis, which is also known as Merrifield method. In some embodiments, the hair growth peptides (HGP) in the present disclosure or in the pharmaceutical composition are purified through protein expression system. The solid phase peptide synthesis is a well-known process and therefore is not discussed in detail. In addition, the HGP of the present disclosure is synthesized by Kelowna Company, which allows persons having ordinary skill in the art to prepare the HGP fragments.

The pharmaceutical composition of the present disclosure can be, but not limited to, a solution dosage form. The HGP is dissolved in 4 ml to 8 ml of Phosphate buffer saline (PBS) solution to form 2 mM HGP solution. In some embodiments, the 2 mM HGP solution is diluted to 0.2 mM HGP solution for the preparation of the pharmaceutical composition of the present disclosure.

The experimental model of the present disclosure is derived from the mouse model of the hair regeneration, which is studied by Dr. Chuong in University of Southern California.

The mouse model adopts female C57BL/6 mice (about 8 weeks).

In accordance with the reports (Muller-Rover et al., 2001; Plikus et al., 2009), after the hair removal on the dorsal skin of the female C57BL/6 mice by wax or uprooting, the hair follicles enter the anagen phase on the seventh day from hair removal. At this time, the dorsal hair will regenerate during the anagen phase, which continues fourteen days. Such step synchronizes all follicles on the dorsal skin.

The hair follicles on the dorsal skin enter the refractory telogen phase through the anagen phase. The refractory telogen phase continues twenty eight days. In the present disclosure, the sample solution is applied on the dorsal skin, where the hair follicle stays at the refractory telogen phase, to observe whether the peptides are beneficial to hair growth.

Figure 1:
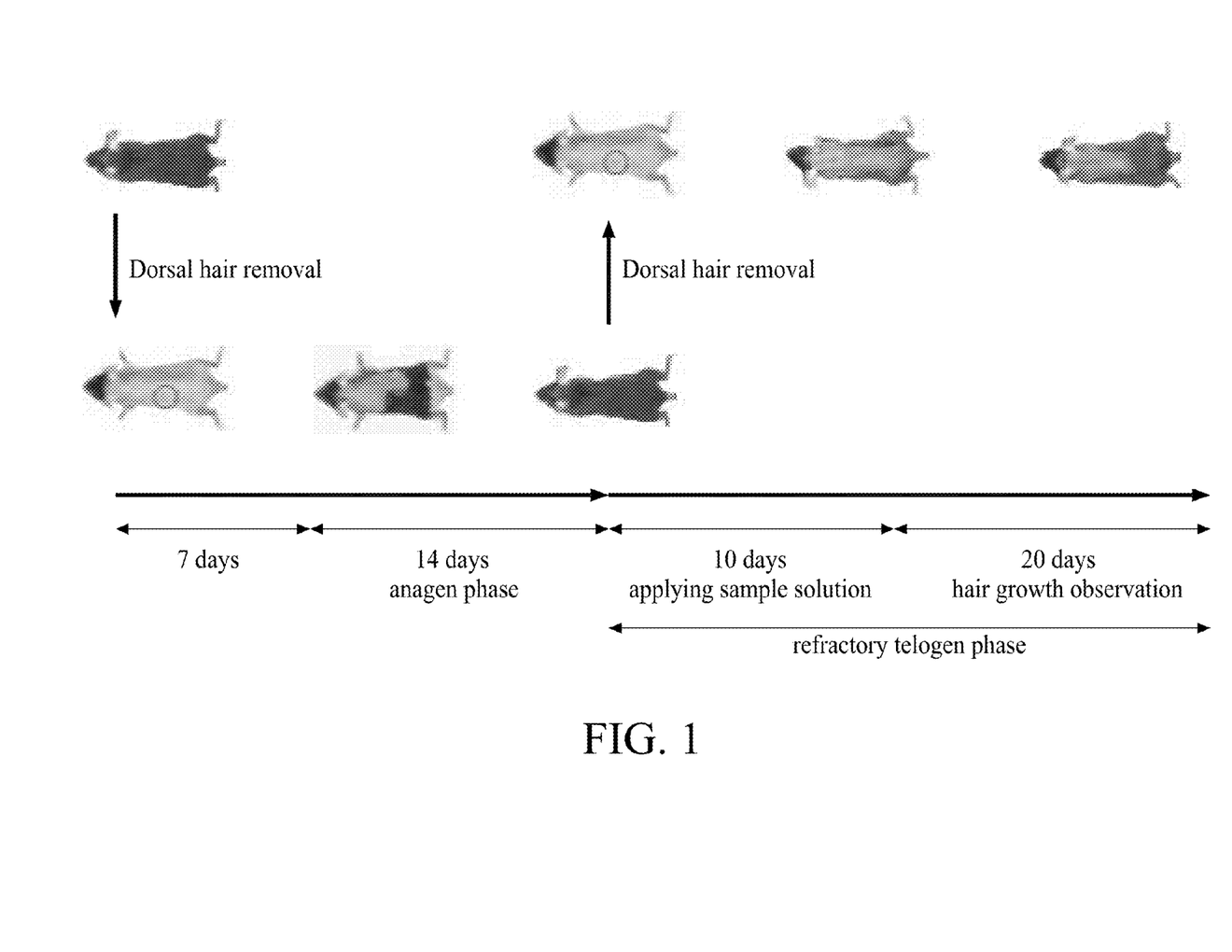
FIG. 1 shows a schematic view of a schedule of an experiment in accordance with an embodiment of the present disclosure.
Figure 2:
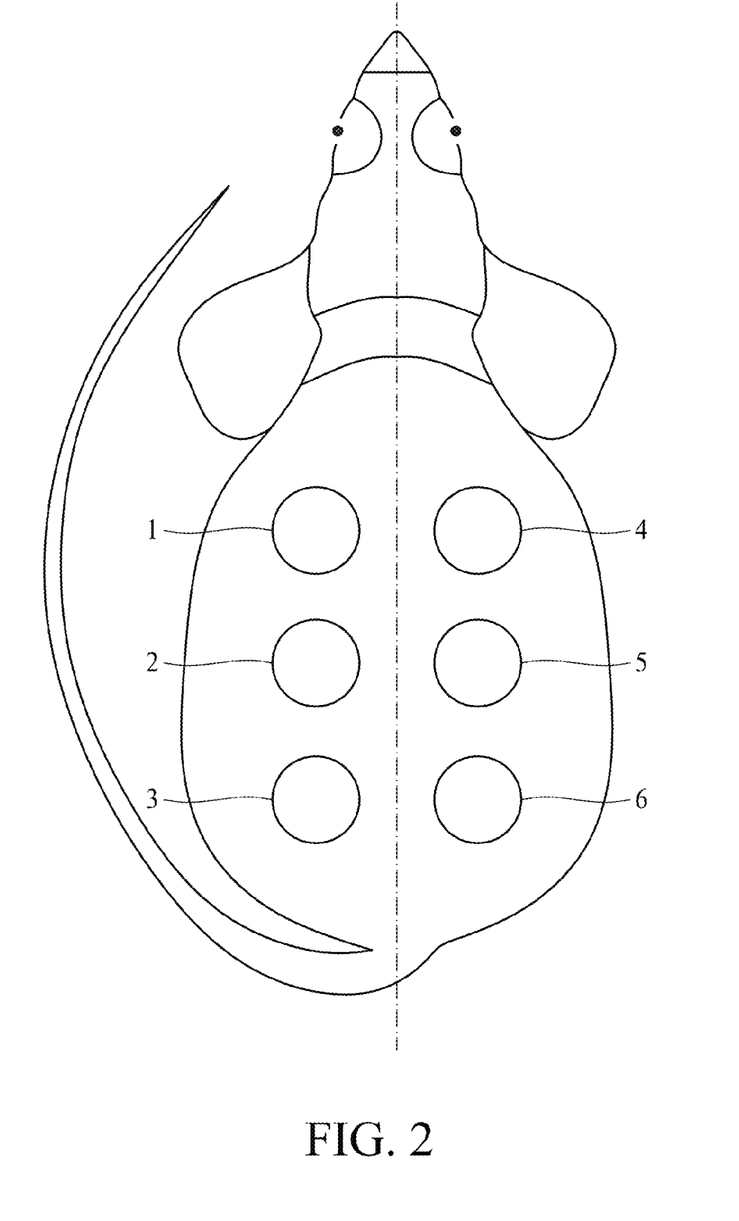
FIG. 2 illustrates a schematic view of six sections on dorsal skin of the mouse in accordance with an embodiment of the present disclosure.

In some embodiments shown in FIG. 1, after the hair removal of the dorsal skin, the new growth hair is removed again at twenty first day after the first hair removal. As shown in FIG. 2, the dorsal skin where the hair is removed is divided into six sections, each of which is spaced apart by 3 centimeters in avoidance of cross-interference. The sample solution is applied on each of the sections for 10 days. The administration of the sample solution includes, but not limited to, the injection (50 μl) and the coating (10 μl). In addition, the dosage of the sample solution includes, but not limited to, the high dosage level (2000 μM) and the low dosage level (200 μM).

In order to avoid experimental error due to manual operation, a positive control and a negative control are predetermined on two sections. For instance, as shown in FIG. 2, the first section 1 is continuously coated with cyclosporine for 10 days (once a day, 10 μl a day). The cyclosporine is regarded as the positive control whose concentration is 0.5% by weight. The solvent of the cyclosporine is 100% alcohol. The second section 2 is coated with high dosage level of HGP or the pharmaceutical composition for 10 days (once a day). The third section 3 is coated with low dosage level of HGP or the pharmaceutical composition for 10 days (once a day). The fourth section 4 is coated with 100% alcohol for 10 days (once a day). The fourth section 4 is regarded as the negative control. The fifth section 5 is continuously injected with the high dosage of HGP or pharmaceutical composition for 10 days (once a day). The sixth section 6 is continuously injected with the low dosage of HGP or pharmaceutical composition for 10 days (once a day). The HGP prepared for the sections is the same amino acid sequence.

In accordance with a report (by Maurer et al., 1997), if the dorsal skin is coated with cyclosporine for 10 days, the hair of the dorsal skin is induced to regenerate. HGP or pharmaceutical composition having the same as referred at Table 1 is implemented through the above-mentioned process and then the hair regeneration condition is recorded every day. Since the period of the refractory telogen phase is 28 days, it is regarded as a negative result that no hair regeneration is observed at thirtieth day after the administration of the sample solution. The negative result means that the peptide cannot improve hair growth. In other words, if the hair regeneration is observed within 30 days after the administration of the sample solution, the peptide or the peptide of the pharmaceutical composition is regarded as HGP, which is able to improve hair growth.

Wnt family has key roles in many developmental processes, including hair follicle growth and differentiation. Canonical Wnt signaling leads to stabilization of β-catenin and accumulation β-catenin, resulting in nuclear translocation and activation of LEF/TCF transcription factors in regulation of gene expression. Wnt/β-catenin signaling has been proposed to function in hair follicle morphogenesis and differentiation (Kishimoto et al. 2000; Fuchs et al. 2001; Millar 2002).

Furthermore, the hair growth cycle is related to Wnt/β-catenin and BMP2/4 signal transduction pathways. Thus, HGP or pharmaceutical composition having the same peptide may control the hair growth through Wnt/β-catenin and BMP2/4 signal transduction pathways. In other words, the HGP or the pharmaceutical composition may affect Wnt/β-catenin and BMP2/4 signal transduction pathways through the hair follicles.

The SEQ ID No. 1 peptide is treated in Human Hair Follicular Keratinocytes (HHFK) and HaCaT Keratinocyte to study the hair growth mechanism induced by the SEQ ID No. 1 peptide.

In the present disclosure, HHFK and HaCaT Keratinocyte are used as cell models for realizing the mechanism. Reporter assay is used as bioactivity assays to identify how the SEQ ID No. 1 peptide improves hair growth.

Figure 3:
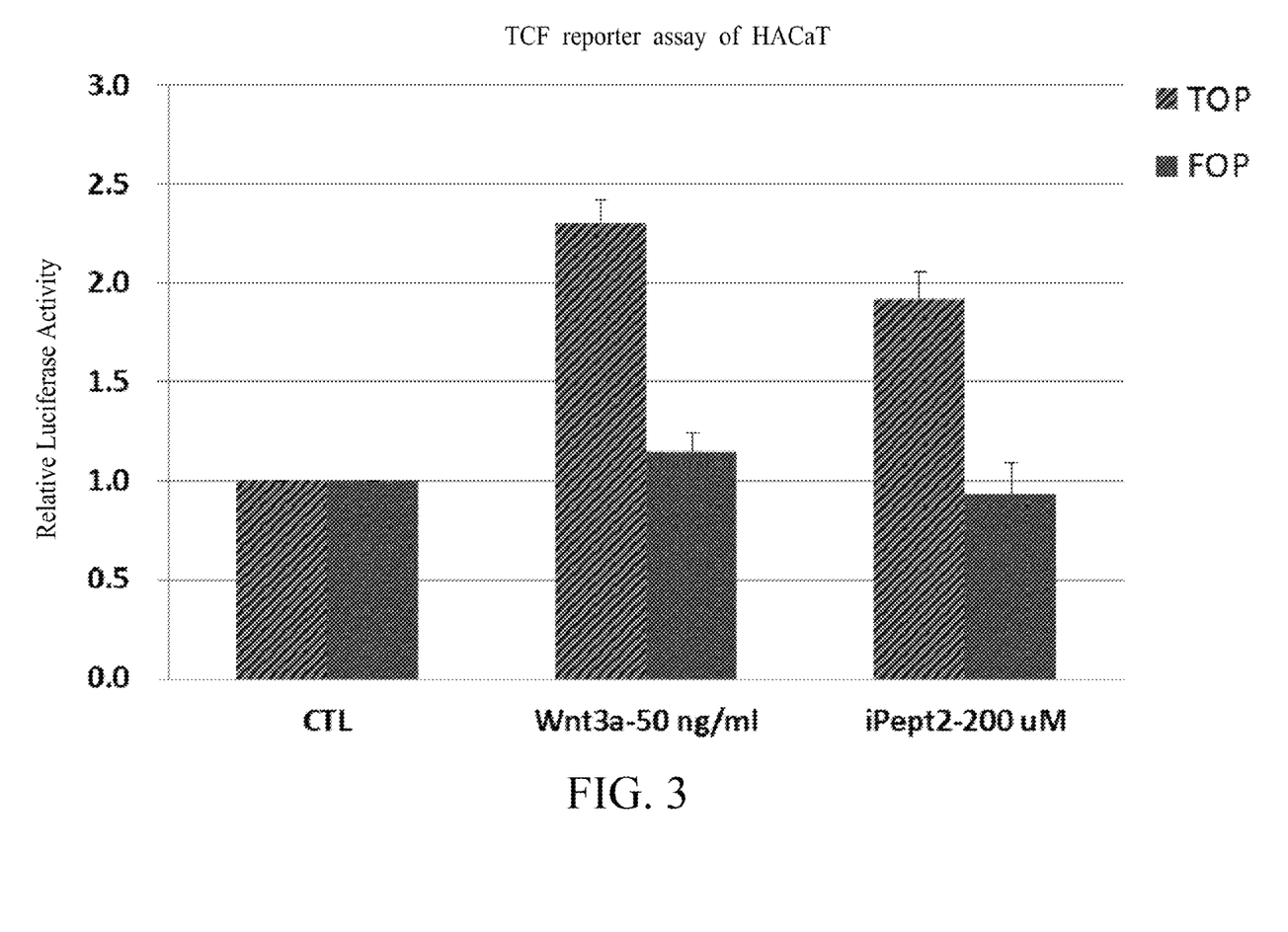
Figure 4:
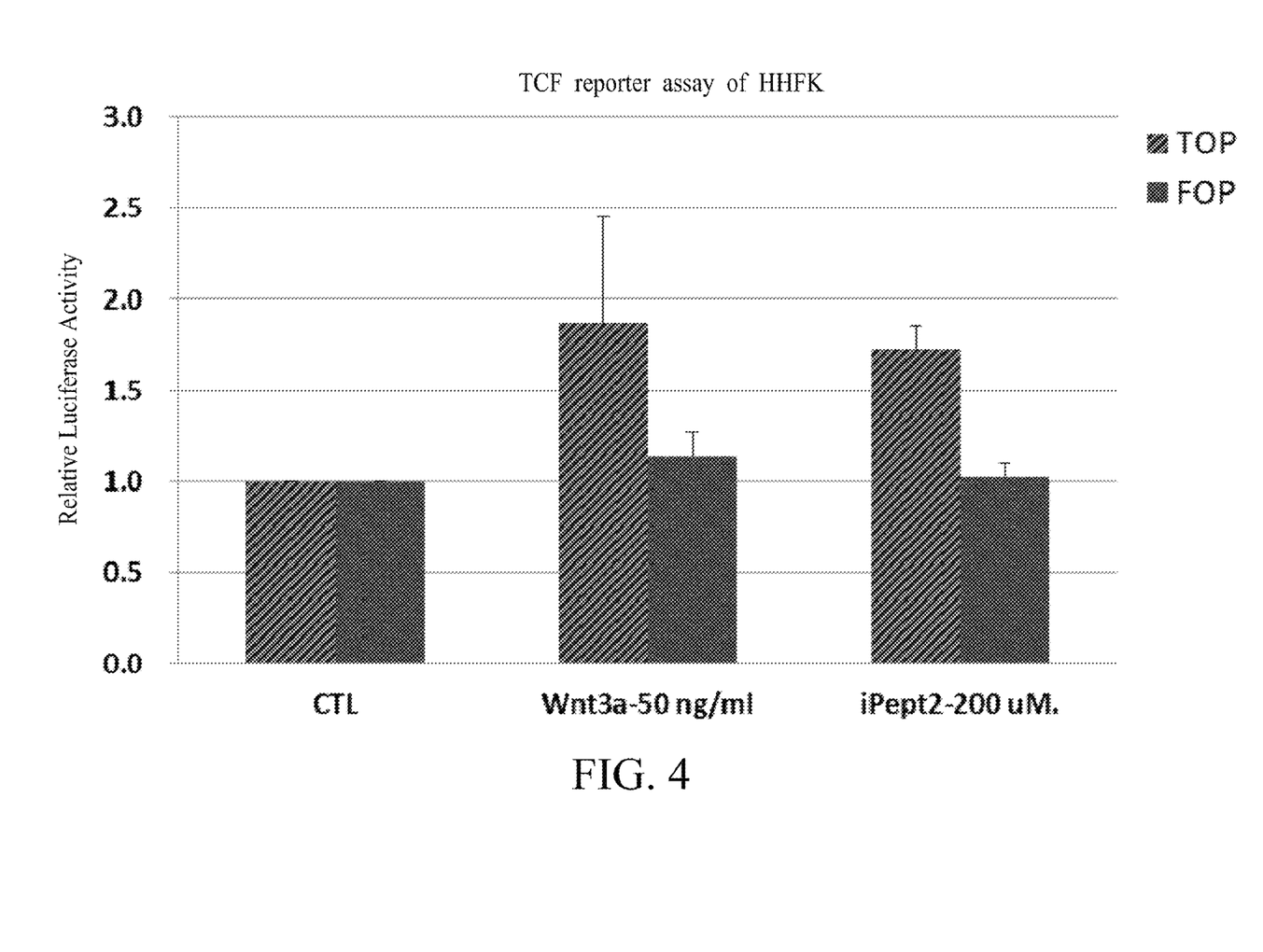
FIG. 4 illustrates a schematic view of a TCF reporter assay in Human Hair Follicular Keratinocytes (HHFK) cell line. TOP represents that the reporter gene has a functional binding site where β-catenin is bound. FOP represents that the functional binding site of the reporter gene is mutated and hence β-catenin cannot bind on the binding site and acts as a negative control. CTL represents that HHFK cell line is not treated with any stimulant. iPept-2 means that HHFK cell line is treated with the SEQ ID No: 1 peptide. In view of the relative luciferase activity, HHFK cell line with the treatment of the SEQ ID No: 1 peptide is observed to increase the activity of β-catenin.

In the reporter assay as shown in FIGS. 3 and 4, a dosage of 50 ng/ml Wnt3a is a positive control. The 200 μM SEQ ID No: 1 peptide is observed to enhance activity of β-catenin in HaCaT and HHFK cells.

Table 1 below lists sequence numbers and their respective amino acid sequences.

TABLE 1

| Sequence number | Amino acid sequence (from amino terminal to carboxyl terminal) | Molecular weight |
| --- | --- | --- |
| SEQ ID No: 1 | SPLAQAVRSSSR | 1258.42 |
| SEQ ID No: 2 | VRSSS | 534.58 |
| SEQ ID No: 3 | SPLAQ | 514.58 |
| SEQ ID No: 4 | SPLAQAVRSSSRTPS | 1543.73 |
| SEQ ID No: 5 | RSSSR | 591.63 |
| SEQ ID No: 6 | SPLAQAVRSSS | 1102.23 |
| SEQ ID No: 7 | SPLAQAVRSS | 1015.15 |
| SEQ ID No: 8 | SPLAQAVRS | 928.07 |
| SEQ ID No: 9 | SPLAQAVR | 840.99 |
| SEQ ID No: 10 | SPLAQAV | 684.80 |
| SEQ ID No: 11 | SPLAQA | 585.67 |
| SEQ ID No: 12 | PLAQAVRSSSR | 1171.34 |
| SEQ ID No: 13 | LAQAVRSSSR | 1074.22 |
| SEQ ID No: 14 | AQAVRSSSR | 961.06 |
| SEQ ID No: 15 | QAVRSSSR | 889.98 |
| SEQ ID No: 16 | AVRSSSR | 761.85 |

TABLE 1-continued

| Sequence number | Amino acid sequence (from amino terminal to carboxyl terminal) | Molecular weight |
|---|---|---|
| SEQ ID No: 17 | VRSSSR | 690.77 |
| SEQ ID No: 18 | SPLAQAVRSSSG | 1159.28 |
| SEQ ID No: 19 | SPLAQAVRSSGS | 1159.28 |
| SEQ ID No: 20 | SPLAQAVRSGSF | 1219.38 |
| SEQ ID No: 21 | SPLAQAVRGSFG | 1189.35 |
| SEQ ID No: 22 | SPLAQAVGSFGS | 1120.24 |
| SEQ ID No: 23 | SPLAQAGSFGSF | 1168.29 |
| SEQ ID No: 24 | SPLAQGSFGSFG | 1154.26 |
| SEQ ID No: 25 | SPLAQAVRSSSRTP | 1456.65 |
| SEQ ID No: 26 | SPLAQAVRSSSRT | 1359.53 |
| SEQ ID No: 27 | GPLAQAVRSSSR | 1228.39 |
| SEQ ID No: 28 | GSLAQAVRSSSR | 1218.35 |
| SEQ ID No: 29 | GSFAQAVRSSSR | 1252.37 |
| SEQ ID No: 30 | GSFGQAVRSSSR | 1238.34 |
| SEQ ID No: 31 | GSFGSAVRSSSR | 1197.29 |
| SEQ ID No: 32 | GSFGSFVRSSSR | 1273.39 |
| SEQ ID No: 33 | SPLAQFRSSSRG | 1292.43 |
| SEQ ID No: 34 | LAQAGSVRSSSR | 1218.34 |
| SEQ ID No: 35 | AQAGSFVRSSSR | 1252.36 |
| SEQ ID No: 36 | QAGSFGFRSSSR | 1286.38 |
| SEQ ID No: 37 | AGSFFSGRSSSR | 1245.33 |

Table 2 lists the experimental numbers of HGP and the pharmaceutical composition corresponding to the sequence numbers. The similarity among the sequences of the present disclosure is analyzed by the software shimadu LCMS2010.

TABLE 2

| Experimental number | Sequence number |
|---|---|
| P1 | SEQ ID No: 1 |
| P2 | SEQ ID No: 2 |
| P3 | SEQ ID No: 3 |
| P4 | SEQ ID No: 4 |
| P5 | SEQ ID No: 5 |
| P6 | SEQ ID No: 6 |
| P7 | SEQ ID No: 7 |
| P8 | SEQ ID No: 8 |
| P9 | SEQ ID No: 9 |
| P10 | SEQ ID No: 10 |
| P11 | SEQ ID No: 11 |
| P12 | SEQ ID No: 12 |
| P13 | SEQ ID No: 13 |
| P14 | SEQ ID No: 14 |
| P15 | SEQ ID No: 15 |
| P16 | SEQ ID No: 16 |
| P17 | SEQ ID No: 17 |
| P18 | SEQ ID No: 18 |
| P19 | SEQ ID No: 19 |
| P20 | SEQ ID No: 20 |
| P21 | SEQ ID No: 21 |

TABLE 2-continued

| Experimental number | Sequence number |
|---|---|
| P22 | SEQ ID No: 22 |
| P23 | SEQ ID No: 23 |
| P24 | SEQ ID No: 24 |
| P25 | SEQ ID No: 25 |
| P26 | SEQ ID No: 26 |
| P27 | SEQ ID No: 27 |
| P28 | SEQ ID No: 28 |
| P29 | SEQ ID No: 29 |
| P30 | SEQ ID No: 30 |
| P31 | SEQ ID No: 31 |
| P32 | SEQ ID No: 32 |
| P33 | SEQ ID No: 33 |
| P34 | SEQ ID No: 34 |
| P35 | SEQ ID No: 35 |
| P36 | SEQ ID No: 36 |
| P37 | SEQ ID No: 37 |

The peptides of the experimental numbers P1 to P37 are adopted in the previously discussed processes as illustrated in FIG. 1 and FIG. 2 and the hair growth condition is observed and recorded in the table 3. The number x of the hair growth in the table 3 means that the hair regeneration condition is observed at the x'th day after the high dosage level is administrated on the dorsal skin. For instance, the number (x=5) means that the hair growth is observed at the fifth day. Furthermore, the symbol NA represents the need for further analysis. Furthermore, each of the number x is verified by the positive control, where the hair regeneration is observed within 30 days. In addition, the "negative" represents no hair growth by using the peptide in accordance with the experimental number.

TABLE 3

| Experimental number | Number x |
|---|---|
| P1 | 22 |
| P2 | negative |
| P3 | 22 |
| P4 | 22 |
| P5 | 22 |
| P6 | negative |
| P7 | 22 |
| P8 | negative |
| P9 | 19 |
| P10 | 22 |
| P11 | 22 |
| P12 | 22 |
| P13 | 22 |
| P14 | 22 |
| P15 | negative |
| P16 | negative |
| P17 | negative |
| P18 | negative |
| P19 | negative |
| P20 | negative |
| P21 | negative |
| P22 | negative |
| P23 | negative |
| P24 | negative |
| P25 | negative |
| P26 | negative |
| P27 | 22 |
| P28 | negative |
| P29 | 22 |
| P30 | negative |
| P31 | 22 |
| P32 | negative |
| P33 | negative |
| P34 | negative |
| P35 | negative |

TABLE 3-continued

| Experimental number | Number x |
|---|---|
| P36 | negative |
| P37 | 22 |

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present disclosure is not intended to be limited to the particular embodiments of the process, sequence, peptide, and composition of matter, means, methods and steps described in the specification. As one of ordinary skill in the art will readily appreciate from the disclosure of the present disclosure, processes, sequence, peptide, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, sequence, peptide, compositions of matter, means, methods, or steps. It will be apparent to those skilled in the art that various modifications and variations can be made to the disclosed embodiments. It is intended that the specification and examples be considered as exemplary only, with a true scope of the disclosure being indicated by the following claims and their equivalents

What is claimed is:

1. A pharmaceutical composition for hair growth comprising:
   a hair growth peptide, wherein the hair growth peptide is selected from the group consisting of SEQ ID NO: 27, SEQ ID NO: 29, SEQ ID NO: 31 and SEQ ID NO: 37; and
   a phosphate salt.

2. A method for hair growth, comprising administering a peptide to a subject in need thereof, wherein the peptide is a hair growth peptide (HGP), the hair growth peptide is selected from the group consisting of SEQ ID NO:27, SEQ ID NO:29, SEQ ID NO:31 and SEQ ID NO:37.

3. The method according to claim 2, wherein the hair growth peptide ranges from 200 μM to 2000 μM.

4. The method according to claim 1, wherein the hair growth peptide is applied on a hair follicle.

* * * * *